United States Patent
Tepper et al.

[11] Patent Number: 5,833,611
[45] Date of Patent: Nov. 10, 1998

[54] REAL-TIME ENDOVAGINAL SONOGRAPHY GUIDANCE OF INTRA-UTERINE PROCEDURES

[76] Inventors: Ron Tepper, 3 Hamatmid, 46407 Herzlia, Israel; Ron Hadani, 417 Rutland Ave., Teaneck, N.J. 07666

[21] Appl. No.: 896,052

[22] Filed: Jul. 17, 1997

[51] Int. Cl.$^6$ .................................................. A61B 8/12
[52] U.S. Cl. ........................................................ 600/462
[58] Field of Search ................................... 600/184, 188, 600/201, 210, 461; 128/20

[56] References Cited

U.S. PATENT DOCUMENTS

| | | | |
|---|---|---|---|
| 3,709,215 | 1/1973 | Richmond | 128/20 |
| 4,742,829 | 5/1988 | Law et al. | 600/461 |
| 4,877,033 | 10/1989 | Seitz, Jr. | 600/441 |
| 5,090,414 | 2/1992 | Takano | 600/461 |
| 5,529,571 | 6/1996 | Daniel | 600/210 |
| 5,562,679 | 10/1996 | Valtchev | 600/201 |

*Primary Examiner*—Marvin M. Lateef
*Assistant Examiner*—Maulin Patel
*Attorney, Agent, or Firm*—Mark M. Friedman

[57] ABSTRACT

Apparatus and method for real-time endovaginal sonography guidance of intra-uterine and cervical procedures are provided. The apparatus comprises an assembly, including: (a) an endovaginal ultrasound transducer for insertion into a portion of a patient's vagina; (b) a cervical holder, including: (i) two arms having a securing member; and (ii) two holders, the holders for holding the patient's cervix; and (c) a connector for connecting the ultrasound transducer to the cervical holder, the ultrasound transducer featuring substantially small diameter for allowing a surgeon to perform the procedure. The method comprises: (a) holding a patient's cervix by means of a cervical holder(a) inserting an endovaginal ultrasound transducer into a portion of the patient's vagina, the ultrasound transducer and the cervical holder being inter-connected by means of a connector; (c) performing the procedure; and (d) monitoring the procedure by means of the ultrasound transducer. According to another embodiment, the method comprises: (a) inserting an image transmitting device into a patients uterine cavity; (b) inserting an endovaginal ultrasound transducer into a portion of the patient's vagina, the ultrasound transducer and the image transmitting device being inter-connected by means of a connector; (c) performing the procedure; and (d) monitoring the procedure by means of the ultrasound transducer and the image transmitting device.

11 Claims, 3 Drawing Sheets

REAL-TIME ENDOVAGINAL SONOGRAPHY GUIDANCE OF INTRA-UTERINE PROCEDURES

FIELD AND BACKGROUND OF THE INVENTION

The present invention relates to apparatus and method for real-time endovaginal sonography guidance of intra-uterine and cervical procedures.

Endovaginal ultrasound transducers for diagnosis and monitoring of obstetric and gynecologic disorders are well known in the art. However, the use of such endovaginal probes for real-time monitoring of surgical procedures is very limited.

Examples of endovaginal ultrasound transducers for real-time monitoring and guidance of surgical procedures are disclosed in U.S. Pat. Nos. 4,497,325, 4,671,292, 4,681,103, 4,742,829, 4,877,033, 4,883,059 and 5,280,427.

Most of these disclosures provide ultrasound transducers including a needle and/or catheter guide attached thereto for introducing a needle and/or catheter to a targeted tissue. However, the surgical procedures which may be carried out by such endovaginal probes are usually very limited and include puncturing and drainage of abscesses, local tissue sampling and fluid collection.

The prior art fails to provide endovaginal apparatus and method for real-time monitoring and guidance of more complicated surgical procedures. In particular, the prior art fails to provide endovaginal apparatus and method for real-time monitoring and guidance of intra-uterine and cervical procedures requiring manual dexterity of a surgeon, such as: curettage or evacuation of the uterine cavity for diagnostic and/or therapeutic purposes; removal of an endometrial polyp or submucous myoma; introduction or extraction of an intra-uterine contraceptive device; and systematic sampling of the endometrium and/or the endocervix for diagnostic purposes.

Transabdominal ultrasound is regularly not used for real-time monitoring and guidance of such surgical procedures due to its relatively limited resolution, the need to keep the patient's urinary bladder full during operation, and the need of extra-operating stuff.

As a consequence, such surgical procedures are currently carried out blindly, relying solely on the "feel" transmitted through manual manipulation of the instrument and the surgeon's experience. However, when the position or size of the uterus is incorrectly diagnosed by the surgeon, uterine perforation may occur with remarkable ease. The chances of perforation are higher in the presence of cervical stenosis or uterine malignancy (endometrial or sarcoma).

The main dangers of such uterine perforation include bleeding and trauma to the abdominal viscera as well as damage to internal organs such as bowel, omentum, mesentery, ureter and fallopian tube. Thus, exploration of the abdominal cavity by laparoscopy or laparotomy is often needed due to accidental uterine perforation.

Other poor outcomes of blind operation include, for example, failure to completely remove uterine tissues such as placental or fetal tissues, which necessitates a second curettage under general anesthesia.

There is thus a widely recognized need for, and it would be highly advantageous to have, an apparatus and method for real-time endovaginal sonography guidance and monitoring of intra-uterine and cervical surgical and non-surgical procedures.

Specifically, it would be advantageous to have such apparatus and method for real time monitoring and guidance of procedures such as: curettage and evacuation of the uterine cavity; removal of endometrial polyps; insertion and removal of an intra-uterine contraceptive device; and sampling of a targeted portion of the endometrium and the endocervical canal.

It would be further advantageous to have such apparatus and method which enable the surgeon to perform such intra-uterine and cervical procedures safely, conveniently and efficiently. In particular, it would be advantageous to have such apparatus and method which enable to substantially shorten the duration of surgical procedures currently carried out under general anesthesia and to reduce the rate of complications associated with such procedures.

It would be further advantageous to have apparatus and method which enable the surgeon to simultaneously monitor and guide surgical and non-surgical intra-uterine procedures by means of endovaginal sonography and/or intra-uterine endoscopy.

SUMMARY OF THE INVENTION

According to the present invention there is provided apparatus for guidance and monitoring of intra-uterine and cervical procedures. The apparatus comprising an assembly, including: (a) an endovaginal ultrasound transducer for insertion into a portion of a patient's vagina; (b) a cervical holder, including: (i) two arms having a securing member; and (ii) two holders, the holders for holding the patient's cervix; and (c) a connector for connecting the ultrasound transducer to the cervical holder, the ultrasound transducer featuring substantially small diameter for allowing a surgeon to examine the external cervical os and to perform the procedure.

According to further features in preferred embodiments of the invention described below, the connector may include an aperture for accommodating the ultrasound transducer therein. Further, the connector may include an adjustment member for adjusting the orientation of the ultrasound transducer relative to the connector. Further, the connector may include a protrusion for locking the connector between the arms of the cervical holder upon securing of the cervical holder.

The connector and the cervical holder may be integrally made. Alternatively, the connector and the ultrasound transducer may be integrally made.

According to another embodiment, the apparatus comprises an assembly, including: (a) an endovaginal ultrasound transducer for insertion into a portion of a patient's vagina; (b) an image transmitting device for insertion into the patient's uterine cavity; and (c) a connector for connecting the ultrasound transducer to the image transmitting device, the ultrasound transducer featuring substantially small diameter for allowing a surgeon to perform the procedure.

Further according to the present invention there is provided a method for guidance and monitoring of intra-uterine and cervical procedures, comprising: (a) holding a patient's cervix by means of a cervical holder (b) inserting an endovaginal ultrasound transducer into a portion of the patient's vagina, the ultrasound transducer and the cervical holder being inter-connected by means of a connector; (c) performing the procedure; and (d) monitoring the procedure by means of the ultrasound transducer.

According to another embodiment, the method comprises: (a) inserting an image transmitting device into a patients uterine cavity; (b) inserting an endovaginal ultrasound transducer into a portion of the patient's vagina, the ultrasound transducer and the image transmitting device being interconnected by means of a connector; (c) performing the procedure; and (d) monitoring the procedure by means of the ultrasound transducer and the image transmitting device.

The present invention successfully addresses the shortcomings of the presently known configurations by providing apparatus and method for real-time endovaginal sonography guidance and monitoring of intra-uterine and cervical procedures, such as: curettage and evacuation of the uterine cavity; removal of endometrial polyps and fibroids; introduction and extraction of an intra-uterine contraceptive device; and sampling of the endometrium and the endocervical canal.

The present invention discloses novel apparatus and method for real-time endovaginal sonography guidance and monitoring of intra-uterine and cervical procedures. When using an apparatus according to the present invention, the cervical holder and the endovaginal ultrasound transducer are preferably held by one hand of the surgeon so that the other hand is free to conduct the surgical procedure. Since the diameter of the endovaginal ultrasound transducer is substantially small, the surgeon may conveniently introduce a surgical tool such as a curette through the cervix into the uterine cavity of the patient. Thus, the surgical procedure is continuously guided and monitored by means of the endovaginal ultrasound transducer.

When using an embodiment including an image transmitting device, the ultrasound transducer and the image transmitting device are preferably held by one hand of the surgeon so that the other hand is free to conduct the surgical procedure. Thus, the procedure is continuously guided and monitored by means of two complementary methods.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of apparatus and method for real-time endovaginal sonography guidance of intra-uterine and cervical surgical and non-surgical procedures. Specifically, the present invention can be used to guide and monitor intra uterine and cervical procedures such as: curettage or evacuation of the uterine cavity for diagnostic and/or therapeutic purposes; removal of an endometrial polyp or submucous myoma; introduction or extraction of an intra-uterine contraceptive device; sampling of a targeted portion of the endometrium and/or the endocervix for diagnostic purposes; and simultaneous insertion of an image transmitting device such as endoscopy equipment into the uterine cavity for complementary diagnostic and/or therapeutic purposes.

The principles and operation of apparatus and method according to the present invention may be better understood with reference to the drawings and the accompanying description.

Figure 1:
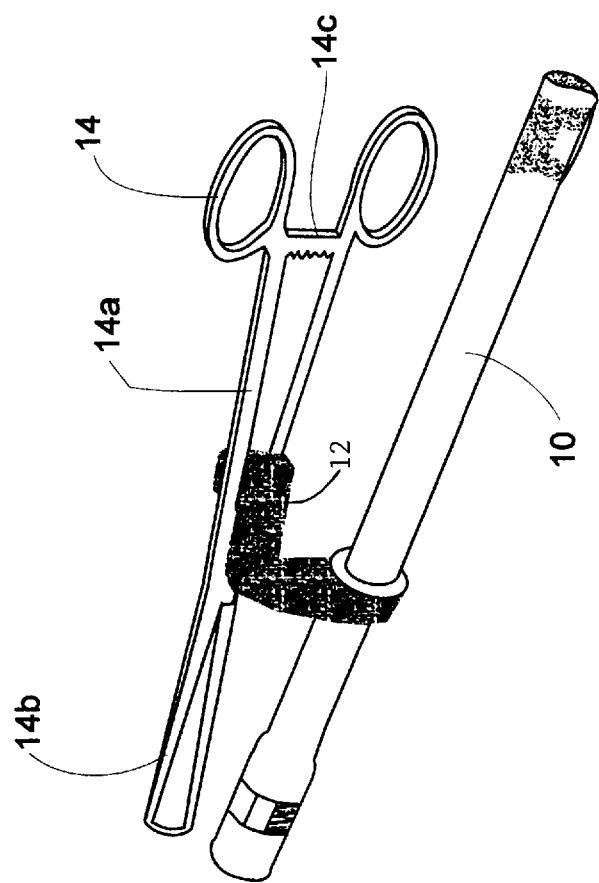
FIG. 1 is a schematic illustration of apparatus according to the present invention.

Referring now to the drawings, FIG. 1 illustrates a preferred embodiment of apparatus according to the present invention. As shown in the figure, the apparatus includes an endovaginal ultrasound transducer 10, a cervical holder 14 and a connector 12 for connecting endovaginal ultrasound transducer 10 to cervical holder 14. Preferably, endovaginal transducer 10 features substantially small diameter so as to allow simultaneous insertion of transducer 10 and cervical holder 14 into the patient's vagina. Cervical holder 14 is preferably a conventional cervical holder, including: two arms 14a including a securing member 14c; and two holders 14b for holding a cervix of a patient.

Figure 2:
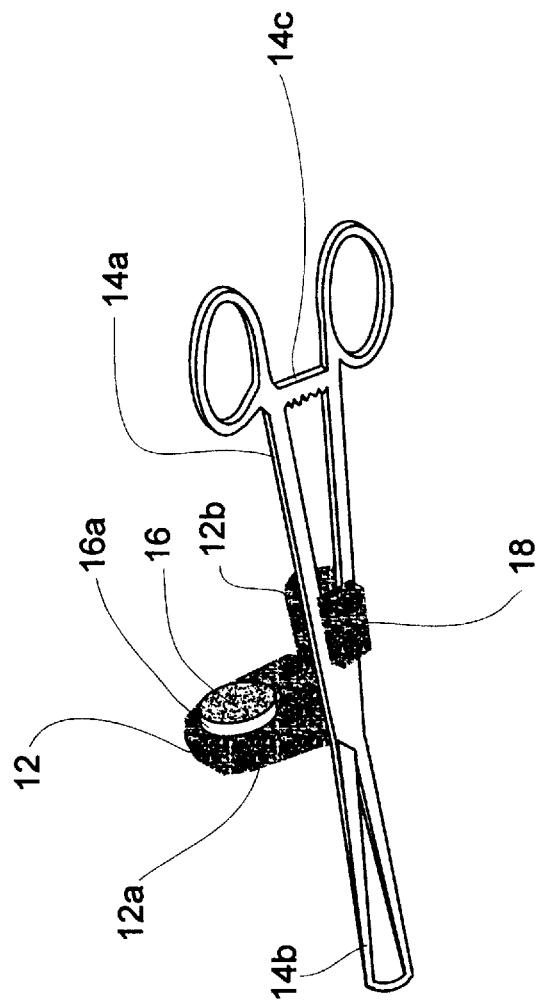
FIG. 2 is a detailed description of a preferred embodiment of a connector according to the present invention.

As shown in FIG. 2, connector 12 preferably includes a first segment 12a and a second segment 12b. Preferably, first segment 12a features a flat configuration and includes a circular aperture 16 for accommodating transducer 10 therein. Preferably, an adjustment annular member 16a is embedded within aperture 16 for adjusting the orientation of transducer 10 relative to first segment 12a. Preferably, second segment 12b features an elongated configuration and includes a protrusion 18 for locking connector 12 between arms 14a, as holders 14b grip the cervix of the patient upon securing of cervical holder 14 by means of securing member 14c. The dimensions of connector 12 may be specifically adapted for various probes. Connector 12 may be made of any appropriate material. Preferably, connector 12 is disposable.

According to another configuration (not shown), connector 12 and cervical holder 14 are integrally made. Alternatively, connector 12 and endovaginal ultrasound transducer 10 are integrally made.

Figure 3:
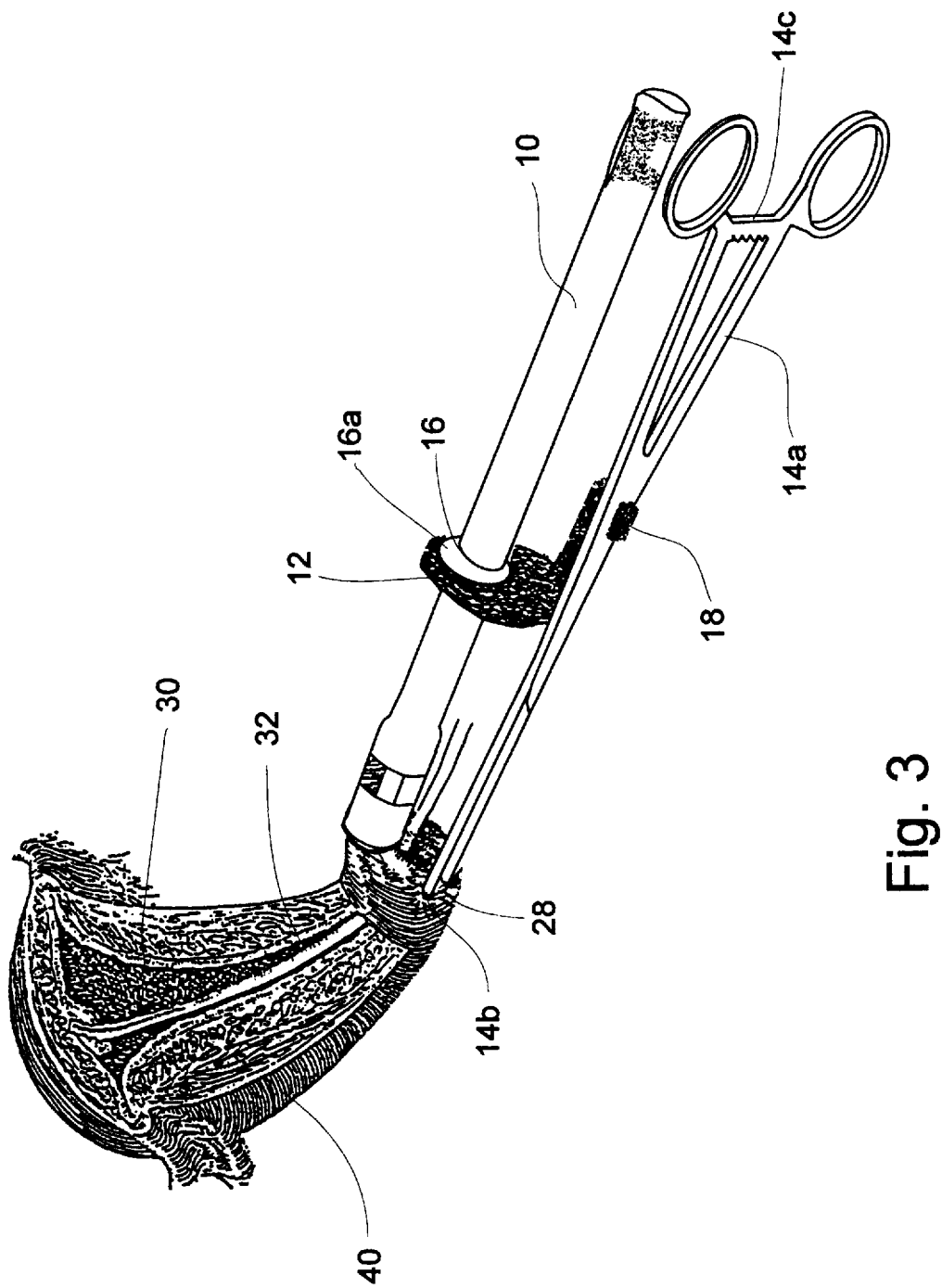
FIG. 3 illustrates the use of the apparatus shown in FIG. 1 for guiding and monitoring intrauterine curettage.

FIG. 3 illustrates the use of an apparatus according to the present invention for monitoring and guiding curettage of a patient's uterus 40. When using the apparatus shown in FIG. 1, endovaginal ultrasound transducer 10 is assembled with connector 12 by inserting transducer 10 into aperture 16 of connector 12. Cervical holder 14 is then used to grip the cervix 28 of a patient by means of holders 14b, such that protrusion 18 of connector 12 is locked between arms 14a when securing the cervical holder. Preferably, endovaginal transducer 10 is then slidably inserted into the fornix of the patient (not shown), and its desired orientation is set so as to allow optimal guidance and monitoring of the intra uterine procedure.

During a uterine procedure, cervical holder 14 and endovaginal ultrasound transducer 10 are preferably held by one hand of the surgeon so that the other hand is free to conduct the surgical procedure. Since the diameter of endovaginal ultrasound transducer 10 is substantially small, the operator may conveniently introduce a surgical tool such as a curette 32 through the cervix 28 into the uterine cavity 30 of the patient. The surgical procedure is then carried out and is continuously guided and monitored by means of endovaginal ultrasound transducer 10. The orientation of transducer 10 relative to connector 12 may be continuously changed as the surgical procedure proceeds.

According to another embodiment (not shown), connector 12 is used to connect endovaginal ultrasound transducer 10 to an image transmitting device for diagnostic and/or therapeutic purposes such that ultrasound transducer 10 is preferably inserted into the patient's fornix and the image transmitting device is preferably inserted through the cervical canal into the uterine cavity. The image transmitting device may be, for example, an optic fiber, or endoscopy equipment. The image transmitting device may include an image transmitting element such as a CCD or a video camera.

Thus, for example, transducer 10 may be connected by means of connector 12 to an endoscopy equipment so as to allow simultaneous monitoring of the surgical procedure by means of two complementary methods, thereby enabling to accurately determine the position of a surgical tool with relation to the uterine wall.

While the invention has been described with respect to a limited number of embodiments, it will be appreciated that many variations, modifications and other applications of the invention may be made.

What is claimed is:

1. An apparatus for guidance and monitoring of intra-uterine and cervical procedures, comprising an assembly, including:
   (a) an endovaginal ultrasound transducer being adapted for insertion into a portion of a patient's vagina;
   (b) a cervical holder, including: (i) two arms having a securing member; and (ii) two holders, said holders being for holding the patient's cervix; and
   (c) a connector for interconnecting said ultrasound transducer and said cervical holder.

2. The apparatus of claim 1, wherein said connector includes an aperture for accommodating said ultrasound transducer therein.

3. The apparatus of claim 1, wherein said connector includes an adjustment member for adjusting the orientation of said ultrasound transducer relative to said connector.

4. The apparatus of claim 1, wherein said connector includes a protrusion for locking said connector between said arms of said cervical holder upon securing of said cervical holder by means of said securing member.

5. The apparatus of claim 1, wherein said connector and said cervical holder are integrally made.

6. The apparatus of claim 1, wherein said connector and said ultrasound transducer are integrally made.

7. A method of guidance and monitoring of intra-uterine and cervical procedures, comprising:
   (a) holding a patient's cervix by a cervical holder;
   (b) inserting an endovaginal ultrasound transducer into a portion of the patient's vagina, said ultrasound transducer and said cervical holder being inter-connected by a connector;
   (c) performing the procedure, while holding the patient's cervix by said cervical holder; and
   (d) real-time monitoring the procedure by said ultrasound transducer.

8. The method of claim 7, wherein said procedure includes inserting an image transmitting device into the patient's uterine cavity and monitoring the procedure by said image transmitting device.

9. The method of claim 8, wherein said image transmitting device is an endoscope.

10. The method of claim 8, wherein said image transmitting device includes a CCD.

11. The method of claim 8, wherein said image transmitting device is an optic fiber.

* * * * *